(12) United States Patent
Giannessi et al.

(10) Patent No.: US 7,368,605 B2
(45) Date of Patent: May 6, 2008

(54) VARIOUSLY SUBSTITUTED DERIVATIVES OF GUANIDINE, AND THEIR USE AS MEDICINES WITH ANTI-DIABETES AND/OR ANTI-OBESITY ACTIVITY

(75) Inventors: Fabio Giannessi, Pomezia (IT); Emanuela Tassoni, Pomezia (IT); Maria Ornella Tinti, Pomezia (IT); Pompeo Pessotto, Pomezia (IT); Maurizio Botta, Siena (IT); Pederico Corelli, Siena (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 163 days.

(21) Appl. No.: 10/537,269

(22) PCT Filed: Dec. 1, 2003

(86) PCT No.: PCT/IT03/00792

§ 371 (c)(1),
(2), (4) Date: Jul. 19, 2005

(87) PCT Pub. No.: WO2004/054967

PCT Pub. Date: Jul. 1, 2004

(65) Prior Publication Data

US 2006/0069100 A1    Mar. 30, 2006

(30) Foreign Application Priority Data

Dec. 17, 2002 (IT) .......................... RM2002A0625

(51) Int. Cl.
*C07C 277/00* (2006.01)
*A01N 37/52* (2006.01)

(52) U.S. Cl. ...................... 564/230; 514/415; 514/634; 548/483

(58) Field of Classification Search ............... 564/230; 548/483; 514/415, 634
See application file for complete search history.

(56) References Cited

U.S. PATENT DOCUMENTS 4,731,383 A * 3/1988 Erczi et al. ................. 514/634

FOREIGN PATENT DOCUMENTS

WO          93/03714       3/1993
WO       WO 97/23203   *   7/1997

OTHER PUBLICATIONS

International Search Report for PCT/IT03/00792 dated Apr. 26, 2004.
Wilkinson-Berka, et al., *ALT-946 and Aminoguanidine, Inhibitors of Advanced Glycation, Improve Severe Nephropathy in the Diabetic Transgenic (mREN-2)27 Rat*, Diabetes, vol. 51, Nov. 2002, XP-002276482, pp. 3283-3289.

* cited by examiner

*Primary Examiner*—Yvonne Eyler
*Assistant Examiner*—Yate' K Cutliff
(74) *Attorney, Agent, or Firm*—Nixon & Vanderhye P.C.

(57) ABSTRACT

Formula (I) compounds

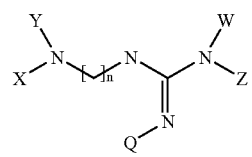

are described where the groups are as identified in the text, and their use as medicines, particularly as anti-diabetes, serum glucose-lowering and anti-obesity agents. They are useful for the prophylaxis and treatment of diabetes, particularly type 2 diabetes, and its complications, syndrome X, the various forms of insulin resistance, and hyperlipidaemias, as well as for the treatment of obesity.

10 Claims, No Drawings

VARIOUSLY SUBSTITUTED DERIVATIVES OF GUANIDINE, AND THEIR USE AS MEDICINES WITH ANTI-DIABETES AND/OR ANTI-OBESITY ACTIVITY

This application is the U.S. national phase of international application PCT/IT2003/000792 filed 1 Dec. 2003, which designated the U.S. and claims benefit of IT RM2002A000625, filed 17 Dec. 2002, the entire contents of each of which are hereby incorporated by reference.

The invention described herein relates to differently substituted derivatives of guanidine and their use as medicines, particularly those with anti-diabetes and/or anti-obesity activity.

Diabetes is a widespread disease present throughout the world and is associated with major clinical complications including macrovascular damage (atherosclerosis) and microvascular damage (retinopathy, nephropathy and neuropathy). These complications are inevitable consequences of the disease and constitute a serious threat to the life and well-being of the individual.

Diabetes is the 4th most common cause of death in the industrialised countries and its incidence is rapidly increasing in the developing countries. It is associated with a variety of abnormalities such as obesity, hypertension and hyperlipidaemia. Different clinical forms of diabetic disease are known, the most common being type 2 and type 1 diabetes. Type 2 diabetes is characterised by a reduced sensitivity to the action of insulin (insulin resistance) and by a reduction in insulin secretion. There have been numerous reports confirming that insulin resistance is involved in many disease conditions other than type 2 diabetes itself, such as dyslipidaemia, obesity, arterial hypertension, etc. The association between insulin resistance and obesity, hypertension and dyslipidaemia is known as syndrome X.

Drugs useful for the treatment of type 2 diabetes are already known.

The sulphonylureas promote the secretion of insulin by the β-cells (*Diabetes Care*, 1992, 15, 737-754) and increase the release of insulin, which is reduced in type 2 diabetes, thus improving the control of postprandial glucose.

Hypoglycaemia is the most common side effect of the sulphonylureas and can be both severe and prolonged. Moreover, in the heart, the sulphonylureas may hamper vasodilation in cases of ischaemia and may sometimes give rise to arrhythmias.

α-Glucosidase inhibitors such as acarbose and voglibose (*Ann. Int. Med.,* 1994, 121, 928-935) aim at solving the problem of postprandial hyperglycaemia by slowing down carbohydrate absorption in the bowel. The substances are competitive inhibitors of gastrointestinal α-glucosidase, an enzyme that splits starch and saccharose into monosaccharides.

The α-glucosidase inhibitors require dosage adjustments for individual patients: the dose has to be high enough to slow down digestion in the small bowel, but also low enough to ensure that digestion is complete prior to entry of carbohydrates into the large bowel (to avoid intestinal side effects). The main side effect reported is flatulence (19%), followed by diarrhoea (3.8%).

The α-glucosidase inhibitors do not relieve the liver production of glucose which is active far from meal times in postabsorption conditions and fasting.

The thiazolidinediones (troglitazone, pioglitazone e rosiglitazone) are oral serum-glucose-lowering drugs which have recently come onto the market with considerable success (*Bioorg. Med. Chem. Lett.,* 1994, 4, 1181-1184).

In 1998 the turnover of troglitazone (Rezulin) *J. Med. Chem.,* 1989, 32, 421-428) in the USA was 748 million dollars, a figure which is only slightly less than the turnover of metformin (Glucophage) which was 861 million dollars and ranks metformin as the best-selling drug among the oral antidiabetes agents on the U.S. market. The thiazolidinediones increase the insulin sensitivity of tissues and are capable of reducing hyperglycaemia and partly diabetic hyperlipidaemia, as well as of reducing insulin levels.

Metformin, which was introduced in Europe in the '50s and in the USA in 1994 is widely used in the treatment of type 2 diabetes and is the drug of choice in the therapy of type 2 diabetes associated with obesity.

Metformin reduces the liver production of glucose (Cusi and De Fronzo, *Diabetes Rev* 6: 89-131, 1998 Hundal et al., *Diabetes* 49: 2063-2069, 2000) and promotes the uptake of glucose stimulated by insulin in muscle (Galuska et al. *Diabetologia* 37: 826-832, 1994; Bailey et al., *N Engl J Med* 334: 574-579, 1996); Kirpichnikov et al., *Ann Intem Med* 137: 25-33, 2002). Its action also affects lipid metabolism through a reduction in levels of free fatty acids and triglycerides in the blood (Cusi et al., *J Clin Endocrinol Metab* 81: 4059-4067, 1996; Kim et al., *Diabetes* 51: 443-448, 2002).

Metformin, moreover, is thought to be capable of restoring insulin secretion impaired by chronic exposure to fatty acids or to high levels of glucose (Patanè et al. *Diabetes* 49: 735-740, 2000) and of inhibiting lipase stimulated by catecholamines in adipose tissue (Flechtner-Mors et al. *Diabetes Med* 16: 1000-1006, 1999).

The molecular action sites of metformin, however, are still largely unclear (Wiernsperger and Bailey, *Drugs* 58: 31-39, 1999; Hundal et al., *Diabetes* 49: 2063-2069, 2000; Musi et al., *Diabetes* 51: 2074-2081, 2002; Hawley et al, *Diabetes* 51: 2420-2425, 2002).

It would appear that the reduction in liver production of glucose induced by metformin is related to a reduction in levels of key enzymes in gluconeogenesis such as glucose-6-phosphatase, phosphoenol-pyruvate kinase, and fructose-1,6-biphosphatase (Fulgencio et al., *Biochem Pharmacol* 62: 439-446, 2001; Song et al., *Am J Phyiol Endocrinol Metab* 281: E275-E282, 2001) and is partly mediated by suppression of oxidation of fatty acids (Perriello et al., *Diabetes* 43: 920-928, 1994). An effect of metformin on NOS (nitric oxide synthetase) has recently been reported in the literature (Kumar V B et al., *Life Science* 69 (23): 2789-2799, 2001), where the authors relate the effect of reducing food consumption to modulation of NOS.

It has, however, been proved that, apart from the mechanisms and processes involved, metformin is capable of improving the use of glucose and the lipid profile, thus reducing insulin resistance (Bailey, *Diabetes Care* 15: 755-772, 1992; Cusi and De Fronzo, *Diabetes Rev* 6: 89-131, 1998). This also emerges from a recent comparison between metformin and the modern thiazolidinediones (Kim et al., *Diabetes* 51: 443-448, 2002; Ciaraldi et al., *Diabetes* 51: 30-36, 2002).

By improving the lipid profile, metformin consequently reduces the cardiovascular risk, and particularly the incidence of myocardial infarction, as demonstrated by the UKPDS study comparing metformin with the sulphonylureas and with insulin (UKPDS Group, *Lancet* 352: 837-853, 1998) and, in addition, the overall mortality in obese diabetic patients (O'Connor et al., *J Fam Pract* 47 Suppl 5: S13-22, 1998).

This aspect which has to do with improving the lipid profile is essential in view of the fact that dyslipidaemia in diabetes increases the risk of cardiovascular damage and the mortality due to cardiovascular damage applies to more than 50% of diabetic patients (Wilson and Poulter U Br *J Bio Med Sci* 58: 248-251, 2001). Metformin reduces hyperglycaemia by 20-30% when it is used as monotherapy after the failure of diet and physical exercise. (UKPDS II, *Diabetes* 34: 793-798, 1985; De Fronzo et al., *J Clin Endocrinol Metab* 73: 1294-1301, 1991; Howlett and Balley, *Drug Saf* 20: 489-503, 1999; Ciaraldi et al., *Diabetes* 51: 30-36, 2002) and by 25% in combination with sulphonylureas (Reaven et al., *J Clin Endocrinol Metab* 74: 1020-1026, 1992). Metformin therapy is limited by the decline in its period of efficacy (Guay, *Pharmacotherapy* 18: 1195-1204, 1998; Riddle, *Am J Med* 108 Suppl 6a: S15-S22, 2000); Carpentier, *Diabetes Metab Res Rev* 18 Supl 3: S70-S76, 2002).

Also worthy of note as side effects are gastrointestinal disorders which have a high incidence (approximately 20%) and reduce patient compliance.

Moreover, metformin cannot be used in conditions where it is contraindicated or where there is a risk or need for caution with its use owing to kidney damage, cardiac insufficiency, chronic lever damage, proteinuria, peripheral vascular damage or lung damage.

From what has been said here above it emerges that the strategies aimed at controlling glucose homeostasis in type 2 diabetes differ one from another and correspond to the different abnormalities present in the diabetic condition.

It has now been found that the compounds with formula (I) described here below are active as serum-glucose-lowering and appetite-lowering agents and are endowed with low toxicity and are therefore useful as medicines, particularly for the treatment of hyperglycaemia and obesity.

Preferred applications are the prophylaxis and treatment of diabetes, particularly type 2, and its complications, syndrome X, various forms of insulin resistance and obesity.

The object of the present invention are compounds with formula (I):

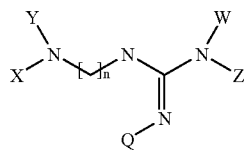

in which:

Z may be selected from: H; saturated or unsaturated, straight or branched alkyl, consisting of 1 to 7 carbon atoms, possibly substituted with alkoxy and halogens; aryl or heteroaryl, mono- or bicyclic, containing one or more heteroatoms selected from the group consisting of nitrogen, oxygen and sulphur, possibly substituted with halogens, $NO_2$, OH, alkyls and alkoxy possibly substituted with halogens; arylalkyl or heteroarylalkyl, where the saturated or unsaturated alkyl residue consists of from 1 to 7 carbon atoms, mono- or bicyclic, containing one or more heteroatoms selected from the group consisting of nitrogen, oxygen and sulphur, possibly substituted with halogens, $NO_2$, OH, carboxy, alkyls and alkoxy, possibly substituted with halogens; or, together with W, may form a cycle, possibly containing one or more heteroatoms;

W may be equal to H or, together with Z, may form a cycle, possibly containing one or more heteroatoms;

n=0-10;

Q may be selected from the Z groups listed above;

X and Y may be the same or different and may be selected from the Z groups listed above;

in addition, X may be a substituted amino-imino of the type:

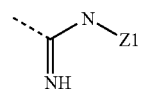

where Z1 may be selected from the Z groups listed above;
or X may be an R—CO group and form a group with nitrogen:

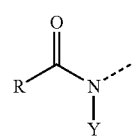

where R can be selected from the Z groups listed above, or —OZ or —NZ;

when n=0, the X—N—Y group can be replaced by an H;

and their pharmacologically acceptable salts, the racemic mixtures, the single enantiomers, stereoisomers or geometric isomers and tautomers;

with the proviso that the formula (I) compound is not N-(4-aminobutyl)-N'-(γ,γ-dimethylallyl)guanidine methane sulphonate (ST2369) or N-(γ,γ-dimethylallyl)guanidine methane sulphonate (ST 2527).

These latter two compounds (ST2369 e ST2527) are compounds known to be useful as hypotensive agents prepared with the procedure described in *J. Med. Chem.*, 44, 2001, 2950-2958 and in *Bioorg. Med. Chem. Letters*, 2, 1992 415-418.

A further object of the present invention is the use of said formula (I) compounds as medicines.

A further object of the present invention are pharmaceutical compositions that contain as their active ingredient one or more formula (I) compounds and at least one pharmacologically acceptable excipient and/or diluent.

Among the formula (I) compounds, those preferred are compounds with the saturated or unsaturated alkyl Z group which may consist of from 1 to 7 carbon atoms and the compounds in which Z is an arylalkyl, with the aryl possibly substituted with one or more halogen atoms. Preferably, the alkyl bound to the aryl to form the arylalkyl group consists of a number of carbon atoms ranging from 1 to 5.

Particularly preferred are the compounds where X and Y are equal to hydrogen and where n is equal to 4-7.

Particularly preferred are the following compounds:

i. N-(6-aminohexyl)-N'-(γ,γ-dimethylallyl)guanidine methane sulphonate (ST2370);

ii. N-(4-aminobutyl)-N'-(3-phenylpropyl)guanidine (ST2521);

iii. N-(4-aminobutyl)-N'-(4-fluorobenzyl)guanidine dichlorhydrate (ST2524);

iv. N-allyl-N'-(4-aminobutyl)guanidine dichlorhydrate (ST2525);

v. 1,4-bis-[N-(γ,γ-dimethylallyl)guanidino]-butane dimethane sulphonate (ST2526);

vi. N-(4-fluorofenil)-N'-(6-amminoesil)-)-4-metil-1-piperazinocarbossimmidammide (ST 2601);

vii. N-(4-fluorofenil)-N'-(6-amminoesil)-1-piperidinocarbossimmidammide (ST 2602);

viii. N-(4-fluorofenil)-N'-(4-amminobutil)-4-metil-1-piperazinocarbossimmidammide (ST2658);
ix. N-(γ,γ-dimetilallil)-N'-(5-amminopentil)guanidina metansolfonata (ST2574);
x. N-(γ,γ-dimetilallil)-N'-(7-amminoeptil)guanidina metansolfonata (ST2575).

A further object of the present invention is the use of the formula (I) compounds:

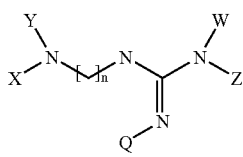

in which:

Z may be selected from: H; saturated and unsaturated, straight or branched alkyl, consisting of from 1 to 7 carbon atoms, possibly substituted with alkoxy and halogens; mono- or bicyclic aryl or heteroaryl, containing one or more heteroatoms selected from nitrogen, oxygen and sulphur, possibly substituted with halogens, $NO_2$, OH, alkyls and alkoxy, possibly substituted with halogens; arylalkyl or heteroarylalkyl, where the saturated or unsaturated alkyl residue consists of from 1 to 7 mono- or bicyclic carbon atoms, containing one or more heteroatoms selected from nitrogen, oxygen and sulphur, possibly substituted with halogens, $NO_2$, OH, carboxy, alkyls and alkoxy, possibly substituted with halogens; or, together with W, may form a cycle, possibly containing one or more heteroatoms;

W may be equal to H or, together with Z, may form a cycle, possibly containing one or more heteroatoms;

n=0-10;

Q may be selected from the Z groups listed above;

X and Y may be the same or different and may be selected from the Z groups listed above;

in addition, X may be a substituted amino-imino of the type:

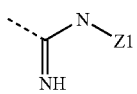

where Z1 may be selected from the Z groups listed above,
or X may be an R—CO group and form a group with nitrogen:

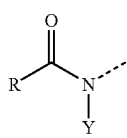

where R may be selected from the Z groups listed above or —OZ or —NZ;
when n=0,
the X—N—Y group may be replaced by an H;
and their pharmacologically acceptable salts, the racemic mixtures, the single enantiomers, stereoisomers or geometric isomers and tautomers, for the preparation of a medicine for the prophylaxis and treatment of hyperglycaemias, particularly for the prophylaxis and treatment of diabetes, preferably type 2 diabetes, and its complications, syndrome X, various forms of insulin resistance, obesity and hyperlipidaemias.

Particularly preferred are the following compounds:

i. N-(6-aminohexyl)-N'-(γ,γ-dimethylallyl)guanidine methane sulphonate (ST2370);
ii. N-(4-aminobutyl)-N'-(3-phenylpropyl)guanidine (ST2521);
iii. N-(4-aminobutyl)-N'-(4-fluorobenzyl)guanidine dichlorhydrate (ST2524);
iv. N-allyl-N'-(4-aminobutyl)guanidine dichlorhydrate (ST2525);
v. 1,4-bis-[N-(γ,γ-dimethylallyl)guanidino]-butane dimethane sulphonate (ST2526);
vi. N-(4-aminobutyl)-N'-(γ,γ-dimethylallyl)guanidine methane sulphonate (ST2369);
vii. N-(γ,γ-dimethylallyl)guanidine methane sulphonate (ST2527);
viii. N-(4-fluorofenil)-N'-(6-amminoesil)-)-4-metil-1-piperazinocarbossimmidammide (ST 2601);
ix. N-(4-fluorofenil)-N'-(6-amminoesil)-1-piperidinocarbossimmidammide (ST 2602);
x. N-(4-fluorofenil)-N'-(4-amminobutil)-4-metil-1-piperazinocarbossimmidammide (ST2658);
xi. N-(γ,γ-dimetilallil)-N'-(5-amminopentil)guanidina metansolfonata (ST2574);
xii. N-(γ,γ-dimetilallil)-N'-(7-amminoeptil)guanidina metansolfonata (ST2575).

Among the formula (I) compounds, those preferred are the compounds with the saturated or unsaturated alkyl Z group which may contain from 1 to 7 carbon atoms and the compounds in which Z is an arylalkyl, with the aryl possibly substituted with one or more halogen atoms. Preferably, the alkyl bound to the aryl to form the arylalkyl group consists of a number of carbon atoms ranging from 1 to 5.

Particularly preferred are the compounds where X and Y are equal to hydrogen and where n is equal to 4-7.

The compounds with general formula (I) can be prepared starting from commercially available starting compounds or can be prepared according to conventional methods, using the reactions described in General Method A, General Method B and General Method C.

General Method A

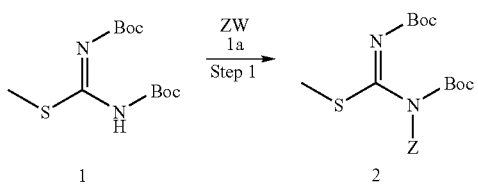

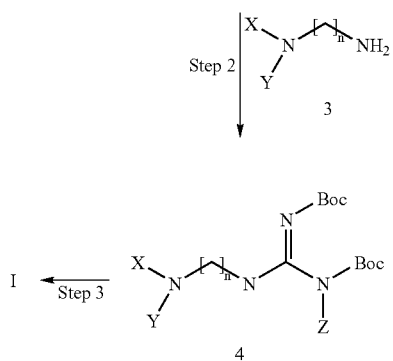

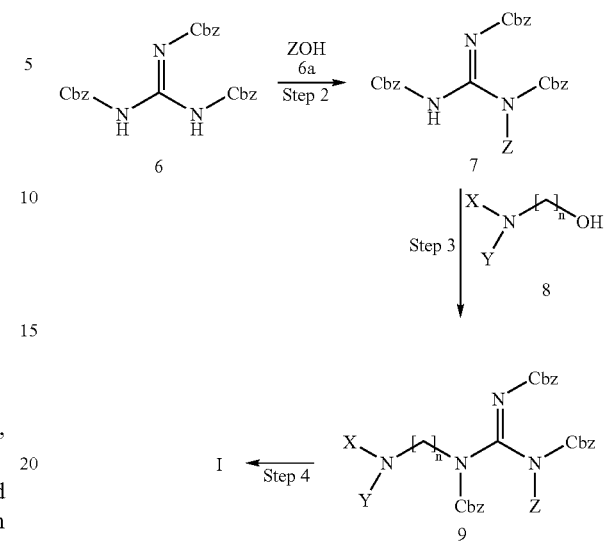

W=an exit group such as halogen, p-toluene sulphonate, or methane sulphonate

The compounds of general formula (I) can be synthesized according to the scheme described above starting from formula 1 and 1a compounds (Step 1), in a ratio of from 1:1.5 to 1:3 equivalents, preferably 1:2.4, where W is a leaving group such as, for example, halogen, p-toluene sulphonate, or methane sulphonate, in phase transfer conditions using preferably mixtures of pairs of solvents as the solvent, preferably $CH_2Cl_2$ and acetonitrile, preferably in a ratio of 19:1, a temperatures ranging from 5° C. to the boiling point of the mixture, preferably at room temperature, for a reaction time which may range from 2 to 24 hours, preferably 6 hours, in the presence of a catalytic amount of a phase transferer such as tetrabutylammonium bromide, and of an organic base, preferably KOH, in a 2 to 4 equivalent excess, preferably 2.8 equivalents.

In Step 2, the compounds of general formula 2, obtained in Step 1, are reacted with compounds of general formula 3, in ratios of from 1:1 to 1:3, preferably 1:1, in aprotic solvents such as THF, at temperatures ranging from 5° C. to the boiling point of the solvent, preferably 50° C., for reaction times ranging from 1 to 6 hours, preferably 3 hours, to yield compounds of general formula 4.

In Step 3, the general formula I compounds are finally obtained, as salts, by deprotection of the formula 4 compounds, by means of organic or inorganic acids, preferably methane-sulphonic acid or hydrochloric acid, in solvents such as alcohols or dioxane, for time periods ranging from 1 hour to 18 hours, preferably 3-6 hours, at temperatures ranging from 25° C. to the reflux temperature of the solvent, preferably 55° C. or the reflux temperature.

The general formula I compounds can also be synthesized according to general method B, starting from general formula 5 compounds, which are reacted (Step 1) with benzylchloroformiate, in ratio preferably of 1:1, in a dipolar aprotic solvent such as THF, in the presence of a base, preferably hydrides of alkaline metals, at temperatures ranging from −55° C. to −25° C., preferably −45° C., for 1 hour and then at room temperature for a reaction time of 12-48 hours preferably 18 hours, to yield formula 6 compounds.

By reaction of the general formula 6 compounds with an alcohol of general formula 6a, according to the Mitsunobu conditions (Step 2), preferably with triphenylphosphine and DIAD in THF, for time periods ranging from 2 to 18 hours, preferably 12 hours, at temperatures ranging from room temperature to the boiling point of the solvent, preferably at reflux temperature, formula 7 compounds are obtained, which, by reaction with an amine alcohol of general structure 8 (Step 3), in which the X group may also signify benzyloxycarbonyl, again according to the Mitsunobu conditions described above, yield formula 9 compounds. The subsequent deprotection by reduction (Step 4) in the presence of Pd/C, preferably 10%, and cyclohexene, in solvents such as MeOH, at temperatures ranging from 25° C. to the boiling point of the solvent, preferably at reflux temperature, for times ranging from 2 hours to 18 hours, preferably 8 hours, yields general formula I compounds.

General Method B

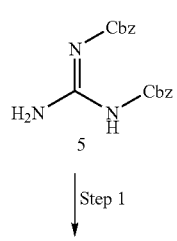

General Method C

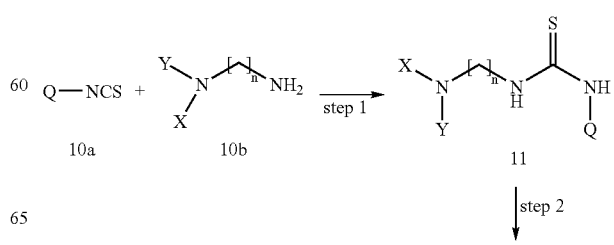

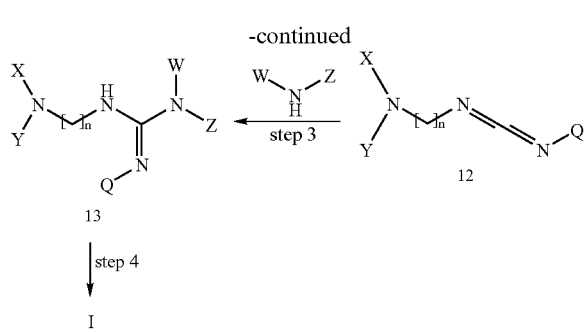

where W=H or, together with Z, forms a cycle, possibly containing one or more heteroatoms.

The general formula I compounds can be synthesised according to the scheme described above starting from compounds of structure 10a and 10b (Step 1), in ratios of from 1:1 to 1:2 equivalents, preferably 1:1.5, by reaction of an amine with an isothiocyanate preferably using $CH_2Cl_2$ as solvent, at temperatures ranging from 5° C. to the boiling point of the solvent, preferably at room temperature, for a reaction time that may range from 2 to 48 hours, preferably 12 hours.

In Step 2, the general formula 11 compounds obtained in Step 1 are transformed into compounds of general structure 12 by reaction with 2-chloro-N-methylpyridinium iodide in amounts ranging from 1.2 to 3.0 equivalents, preferably 1.7 equivalents, in the presence of an organic base, preferably DIPEA in an excess of from 2 to 4 equivalents, preferably 3 equivalents, preferably using $CH_2Cl_2$ as solvent, at temperatures ranging from 5° C. to the boiling point of the solvent, preferably at room temperature.

In Step 3, the compounds of structure 12 are transformed into compounds of structure 13 by reaction with an amine, in a ratio of from 1:1 to 1.2 equivalents, preferably 1.2 equivalents, using toluene as solvent at a temperature ranging from 5° C. to the boiling temperature of the solvent, preferably at 50° C., for a time period ranging from 1 hour to 24 hours, preferably 4 hours.

In Step 4, the general formula I compounds are finally obtained, as salts, by deprotection of formula 13 compounds, by means of organic or inorganic acids, preferably trifluoroacetic acid, in a concentration ranging from 1% to 10%, preferably 5%, in solvents of the $CH_2Cl_2$ type, for a time period ranging from 1 hour to 12 hours, preferably 4 hours, at a temperature ranging from 5° C. to the boiling point of the solvent, preferably room temperature.

EXAMPLE 1

Preparation of N-(γ,γ-dimethylallyl)-N'-(6-aminohexyl)guanidine methane sulphonate ST2370

Preparation of the Intermediate Product N,N'-bis(ter-butoxycarbonyl)-S-methylthiourea The product was prepared starting from S-methylisothiourea sulphate (100 mg, 0.36 mmol) dissolved in $CH_2Cl_2$ (1.5 ml) and $(Boc)_2O$ (314 mg, 1.44 mmol) and 1.44 ml of $NaHCO_3$ sat. sol. as reported in *J. Med. Chem.* 1993, 36, 2956-2963. The reaction mixture was left to stir at room temperature for 18 hours. At the end of this period, $CH_2Cl_2$ (2 ml) was added to the reaction mixture, the organic phase was separated from the aqueous phase and the aqueous phase was extracted with $CH_2Cl_2$. The pooled organic fractions were washed with NaCl s.s. and dried on anhydrous $Na_2SO_4$. The residue was purified by silica gel chromatography using AcOEt/propyl ether 1:3 as eluent to give 105 mg of product as a white solid (yield: 100%). The analytical data were as reported in the literature.

Preparation of the Intermediate Product N-(γ,γ-dimethylallyl)-N,N'-bis(ter-butoxycarbonyl)-S-methylthiourea Method A, Step 1

The product was prepared by adding dropwise to a suspension of KOH (56 mg, 1.00 mmol) and $(n-Bu)_4NBr$ (23 mg, 0.07 mmol) in 6 ml of $CH_2Cl_2/CH_3CN$ 19:1 (solution A) a solution of N,N'-bis(ter-butoxycarbonyl)-S-methylthiourea (105 mg, 0.36 mmol) dissolved in 4 ml of solution A. The reaction mixture was left under stirring for 15 min, after which prenyl bromide (99 mg, 0.86 mmol) dissolved in 20 ml of solution A was added in the space of one hour. The reaction was left under stirring for 6 hours at room temperature.

The solution was diluted with cold water, the two phases were separated and the aqueous phase was extracted with $CH_2Cl_2$, and the pooled organic phases were washed with NaCl s.s. and dried on anhydrous $Na_2SO_4$. After evaporation of the solvent in vacuo, the residue was purified by silica gel chromatography using propyl ether/AcOEt 10:1 as eluent, to give 129 mg of product as a yellow oil, (yield: 100%). IR $(CHCl_3)$ ν 1720,1620 cm-1, $^1$H-NMR $(CDCl_3)$ δ 5.26 ($^1$H, m), 4.12 (2H, d, J=6.5 Hz), 2.36 (3H, s), 1.71, 1.66 (3H each), 1.50, 1.46 (9H each).

Preparation of the Intermediate Product 4-[$N^2$,$N^3$-bis(ter-butoxycarbonyl-$N^3$-(γ,γ-dimethylallyl)-guanidino]-1-aminohexane Method A, Step 2

A solution of N-(γ,γ-dimethylallyl)-N,N'-bis(ter-butoxycarbonyl)-S-methylthiourea (129 mg, 0.36 mmol) in THF (1.6 ml) was added dropwise to a solution of 1,6-diaminohexane (151 mg, 1.3 mmol) in 1 ml of THF. The reaction was brought to 50° C. and kept at that temperature for 3 hours. The reaction mixture was concentrated at reduced pressure and the residue dissolved in a mixture of, $CHCl_3$/ $NaHCO_3$ 10%; the two phases were separated and the aqueous phase extracted with $CHCl_3$. The pooled organic phases were dried on anhydrous $Na_2SO_4$. After evaporation of the solvent in vacuo the residue was purified by chromatography using $CHCl_3/NEt_3$ 5% as eluent to give 154 mg of product as a glassy white solid (yield: 100%). IR $(CHCl_3)$ ν 3250, 1720, 1624 cm$^{-1}$, $^1$H-NMR$(CDCl_3)$ δ 5.15 (1H, t, J=7,1 Hz); 4.20 (2H, d, J=7.1 Hz); 3.25, 2.80 (2H each, J=6.7 Hz); 1.7-1.3 (8H, m); 1.70, 1.66 (3H each); 1.50, 1.46 (9H each).

Preparation of N-(γ,γ-dimethylallyl)-N'-(6-aminohexyl) guanidine methane sulphonate (ST2370)

Method A, Step 3

The product was prepared starting from 4-[$N^2$,$N^3$-bis(ter-butoxycarbonyl-$N^3$-(γ,γ-dimethylallyl)-guanidino]-1-aminohexane (154 mg, 0.36 mmol) dissolved in a solution of methane-sulphonic acid (34.8 mg, 23.5 μL, 0.36 mmol) in anhydrous dioxane (10 ml); the solution obtained was left at reflux temperature in an $N_2$ atmosphere for 3 hours. The solution was cooled and concentrated to dryness in vacuo; the amorphous yellowy-brown solid obtained was washed with ethyl ether, giving 60 mg of product as a rubbery amorphous solid (yield: 52%). $^1$H-NMR$(CD_3OD)$ δ 5.20-5.29 (1H, m), 3.75-3.95 (2H, dd); 3.11-3.24 (4H, m), 2.88-2.99 (4H, m), 2.68 (s, 3H), 1.67-1.86 (6H, m), 1.39-1.49 (4H, m).

EXAMPLE 2

Preparation of N-(4-aminobutyl)-N'-(3-phenylpropyl)guanidine ST2521

Method B, Step 1

Preparation of the Intermediate Product N,N',N"-tris(benzyloxy-carbonyl)guanidine The product was prepared as described in *J.O.C.*, 1998, 63 (23), 8432-8439, starting from a solution of N,N'-bis(benzyloxycarbonyl)guanidine (prepared as described in *J.O.C.*, 1998, 63 (23), 8432-8439), (3 g, 9.17 mmol) in anhydrous THF which was brought to T=−45° C., after which NaH (60% in mineral oil, 728 mg, 18.1 mmol) was added piecemeal in small portions. The suspension was kept at T=−45° C. for 1 hour after which benzylchloroformiate (1.55 g, 9.17 mmol) was added and the suspension was brought back to room temperature in an $N_2$ atmosphere and left under stirring for 18 hours. The mixture was concentrated at reduced pressure, and then diluted with $CH_2Cl_2$ and $H_2O$; the two phases were separated, the organic phase was washed with HCl 1N, NaCl s.s. and dried on anhydrous $Na_2SO_4$. The crude reaction product was purified by silica gel chromatography using $CH_2Cl_2/Et_2O$ as eluent to give 810 mg of product (yield: 19%). Analytical data as reported in the literature.

Preparation of the Intermediate Product N-(cinnamyl)-N,N',N"-tris (benzyloxycarbonyl)guanidine Method B, Step 2

The product was prepared from N,N',N"-tris(benzyloxycarbonyl)guanidine (810 mg, 1.75 mmol) which was solubilised in anhydrous THF (12 ml); to the solution were added $PPh_3$ (298 mg, 1.14 mmol) and cinnamic alcohol (140 mg, 1.05 mmol). The reaction mixture was brought to 0° C. and DIAD (227 mg, 1.14 mmol) was added piecemeal in small portions. On completing the addition, the solution was brought to reflux temperature and kept at that temperature for 12 hours. The reaction was first concentrated at reduced pressure and then diluted with $CHCl_3$ and $H_2O$. The two phases were separated, and the organic phase was washed with NaCl s.s. and dried on anhydrous $Na_2SO_4$. After purification of the residue by silica gel chromatography using propyl ether/AcOEt 4:1 as eluent, 443 mg of product were obtained as a yellow oil (yield: 74%). IR ($CHCl_3$) ν 1760, 1712, 1655, 1615 $cm^{-1}$, $^1H$-NMR ($CDCl_3$) δ 11.11 (brs, 1H); 7.39-7.30 (m, 20H); 6.58 (d, 1H, J=15.8 Hz); 6.30 (dd, 1H, $J^1$=15.7 Hz, $J^2$=6.3 Hz); 5.17 (s, 6H); 4.68 (d, 2H, J=6.2 Hz).

Preparation of N-(4-aminobutyl)-N'-(cinnamyl)-N,N',N",N"'-tetra(benzyloxycarbonyl)guanidine Method B, Step 3

To a solution of N-(cinnamyl)-N,N',N"-tris(benzyloxycarbonyl)guanidine (443 mg, 0.767 mmol) in anhydrous THF (6 ml) were added $PPh_3$ (301 mg, 1.15 mmol) and 4-(N-benzyloxy-carbonyl)aminobutanol (223 mg, 0.998 mmol). The reaction mixture was brought to 0° C. and DIAD (232 mg, 1.15 mmol) was added dropwise. On completing the addition, the reaction was left at reflux temperature for 12 hours. The reaction mixture was first concentrated at reduced pressure and then diluted with $CH_3Cl$ and $H_2O$; the organic phase was separated from the aqueous phase, washed with NaCl s.s. and dried on anhydrous $Na_2SO_4$. After evaporation of the solvent in vacuo, the residue was purified by chromatography using $CH_2Cl_2/Et_2O$ 98:2 as eluent. 176 mg of product were obtained as a yellow oil (yield: 29%). IR ($CHCl_3$) ν 1766, 1722, 1655, 1633 $cm^{-1}$, $^1H$-NMR ($CDCl_3$) δ (ppm) 7.32-7.22 (m, 25H); 6.41 (d, 1H, J=15.8 Hz); 6.16 (dd, 1H, $J^1$=15.8 Hz, $J^2$=6.6 Hz); 5.07-4.96 (m, 8H); 4.23 (d, 2H, J=6.6 Hz); 3.47 (t, 2H, J=6.7 Hz); 2.97 (t, 2H, J=6.1 Hz); 1.47-1.33 (m, 4H).

Preparation of N-(4-aminobutyl)-N'-(3-phenylpropyl)guanidine (ST2521)

Method B, Step 4

The product was prepared by reduction of N-(4-aminobutyl)-N'-(cinnamyl)-N,N',N",N"'-tetra(benzyloxycarbonyl)guanidine (176 mg, 0.225 mmol) solubilised in anhydrous MeOH (20 ml), with Pd/C 10% (215 mg) and cyclohexene (347 mg, 4.5 mmol). The reaction mixture was brought to reflux temperature and kept at that temperature for 8 hours. At the end of this time period the reaction mixture was filtered on celite and washed thoroughly with MeOH. The filtrate was concentrated to dryness in vacuo to give 49 mg of product as a glassy solid (yield: 87.6%). $^1H$-NMR ($CDCl_3$) δ 7.23-7.18 (5H, m), 3.26-3.13 (4H, m), 2.61 (2H, t), 1.90-1.24 (8H, m).

EXAMPLE 3

Preparation of N-(4-aminobutyl]-N'-(4-fluorobenzyl)guanidine dichlorhydrate ST2524

Method A

Preparation of the Intermediate Product N-4-fluorobenzyl-N,N'-bis(ter-butoxycarbonyl)-S-methylthiourea The product was prepared starting from N,N'-bis(ter-butoxycarbonyl)-S-methylthiourea (400 mg, 1.37 mmol), p-fluoro benzylbromide (616 mg, 3.3 mmol) with tetrabutylamonium bromide (82 mg, 0.256 mmol) and KOH (220 mg, 3.93 mmol) in $CH_2Cl_2/CH_3CN$ 19/1 (45 ml) using the same procedure as described for the synthesis of N-(γ,γ-dimethylallyl)-N,N'-bis(ter-butoxycarbonyl)-S-methylthiourea in example 1. 469 mg of amorphous white solid were obtained (yield: 86%). M.p. 156-158° C.; IR ($CHCl_3$) ν 1720, 1625, $^1H$-NMR ($CDCl_3$) δ 7.21 (2H, t); 7.05 (2H, t); 4.76 (2H, s); 1.48-1.54 (s, 9H each).

Preparation of the Intermediate Product 4-[$N^2,N^3$-bis(ter-butoxycarbonyl)-$N^3$-(4-fluorobenzyl)-guanidino]-1-aminobutane The product was prepared starting from N-4-fluorobenzyl-N,N'-bis(ter-butoxycarbonyl)-S-methylthiourea (468 mg, 1.178 mmol), 1,4-diaminobutane (105 mg, 3.07 mmol) in 7 ml of THF using the procedure described for the synthesis of 4-[$N^2,N^3$-bis(ter-butoxycarbonyl-$N^3$-(γ,γ-dimethylallyl)-guanidino]-1-aminohexane in example 1. 116 mg of product were obtained as a yellow oil (yield: 22%). IR ($CHCl_3$) ν 3260, 1720, 1632 $cm^{-1}$, $^1H$-NMR ($CDCl_3$) δ 7.16 (2H, t); 6.84 (2H, t); 4.67 (2H, s); 2.90 (2H, t); 2.44 (2H, t), 1.35-1.19 (22H, m).

Preparation of N-(4-aminobutyl-N'-(4-fluorobenzyl)guanidine dichlorhydrate (ST2524)

The product was prepared starting from 4-[$N^2,N^3$-bis(ter-butoxycarbonyl)-$N^3$-(4-fluorobenzyl)-guanidino]-1-aminobutane (116 mg, 0.26 mmol) solubilised in EtOH (1.5 ml). Every 2 hours 1 ml of HCl 12 N was added; after 4 hours, the solution was left for 15 min at room temperature, and then brought to T=55° C. and kept at that temperature for 6 hours. The solution was concentrated at reduced pressure and the residual aqueous phase was washed with $CH_2Cl_2$ and AcOEt. The aqueous phase was concentrated to dryness in vacuo, giving 46 mg of product as a yellow oil (yield:

57%). $^1$H-NMR (CD$_3$OD) δ 7.31-7.24 (2H, m), 7.03-7.12 (2H, m), 4.34 (2H, s), 3.26 (2H, t), 3.17 (2H, t), 1.58-1.53 (2H, m).

EXAMPLE 4

Preparation of N-allyl-N'-(4-aminobutyl)guanidine dichlorhydrate ST2525

Method A

Preparation of the intermediate product N-allyl-N,N'-bis(ter-butoxycarbonyl)-S-methylthiourea The product was prepared starting from N,N'-bis(ter-butoxycarbonyl)-S-methylthiourea, (1.5 g, 5.1 mmol), distilled allylbromide (1.48 mg, 12.37 mmol), tetrabutylammonium bromide (309 mg, 0.57 mmol), KOH (825 mg, 14.73 mmol) in CH$_2$Cl$_2$/CH$_3$CN 19/1, 99 ml, using the synthesis procedure used for the preparation of N-(γ,γ-dimethylallyl)-N,N'-bis(ter-butoxycarbonyl)-S-methylthiourea in example 1. 950 mg of product were obtained as a white solid (yield: 55%). M.p. 38-40° C.; IR (CHCl$_3$) ν 1720, 1618 cm$^{-1}$; $^1$H-NMR (CDCl$_3$) δ 5.92-5.76 (1H, m), 5.29-5.12 (2H, m), 4.09 (2H,d), 2.34 (3H, s), 1.47-1.43 (9H each).

Preparation of the Intermediate Product 4-[N$^2$,N$^3$-bis(ter-butoxycarbonyl)-N$^3$-(allyl)-guanidino]-1-aminobutane The product was prepared from N-allyl-N,N'-bis(ter-butoxycarbonyl)-S-methylthiourea (950 mg, 2.8 mmol), 1.4 diaminobutane (657 mg, 7.54 mmol) in THF (22 ml) according to the procedure described in example 1. 322 mg of product were obtained as an oil (yield: 32.5%); IR (CHCl$_3$) ν 3256, 1720, 1618 cm$^{-1}$, $^1$H-NMR (CDCl$_3$) δ 5.80-5.72 (1H, m); 5.17-5.04 (2H, m); 4.18 (2H, d); 3.15 (2H, t, J=6.6 Hz); 2.66 (2H; t, J=6.6 Hz); 1.65-1.50 (4H, m); 1.42-1.40 (9H each).

Preparation of N-allyl-N'-(4-aminobutyl)guanidine dichlorhydrate (ST2525)

The product was prepared from 4-[N$^2$,N$^3$-bis(ter-butoxycarbonyl)-N-3-(allyl)-guanidine]-1-aminobutane (322 mg, 0.91 mmol) in EtOH (3 ml) and HCl 12 N (3 ml) using the same procedure described for the synthesis of ST2524 in example 3. 63 mg of product were obtained as a yellow oil (yield: 28.4%). $^1$H-NMR (CD$_3$OD) δ 5.93-5.80 (1H, m); 3.86 (2H, d), 3.29-3.24 (2H, m), 3.05-2.90 (2H, m), 1.85-1.60 (4H, m).

EXAMPLE 5

Preparation of 1,4-bis-[N-(γ,γ-dimethylallyl)guanidino]-butane dimethane sulphonate ST2526

Method A

Preparation of the intermediate product 1,4-bis-[[N$^2$,N$^3$-bis(ter-butoxycarbonyl)N$^3$-(γ,γ-dimethylallyl)guanidino]-butane The product was prepared starting from N-(γ,γ-dimethylallyl)-N,N'-bis(ter-butoxycarbonyl)-S-methylthiourea (493 mg, 1.37 mmol) and 1,4 diaminobutane (48.2 mg, 0.55 mmol) in THF (1.23 ml) as described in the preparation of 4-[N$^2$,N$^3$-bis(ter-butoxycarbonyl-N$^3$-(γ,γ-dimethylallyl)-guanidino]-1-aminohexane in example 1. 195 mg of product were obtained as a colourless oil (yield: 50.2%). IR (CHCl$_3$) ν 1724, 1610 cm$^{-1}$, $^1$H NMR (CDCl$_3$): δ 5.15 (2H, t, J=6.3 Hz), 4.22 (4H, d, J=6.9 Hz) 3.22 (4H, m), 1.66 (12H, d, J=4.7 Hz), 1.58 (4H, m), 1.48 (18H, s), 1.39 (18H, s).

Preparation of 1,4-bis-[N-(γ,γ-dimethylallyl)guanidino]-butane dimethane sulphonate (ST2526)

The product was prepared starting from 1,4-Bis-[[N$^2$,N$^3$-bis(ter-butoxycarbonyl)-N$^3$-(γ,γ-dimethylallyl)guanidino]-butane (195 mg, 0.276 mmol), prepared as described above, and methane-sulphonic acid (53 mg, 0.552 mmol) in dioxane (11 ml), as described in the preparation of ST2370 in example 1. 109 mg of product were obtained as a yellow oil (yield: 78.9%). $^1$H-NMR (CD$_3$OD) 5.31 (2H, m), 3.61 (4H, m), 3.26 (4H, m), 2.72 (6H, s), 1.91-1.72 (12H, m).

EXAMPLE 6

Preparation of N-(4-fluorophenyl)-N'-(6-aminohexyl)-N-(4)-4-methyl-1-piperazinocarboximidamide (ST 2601)

Preparation of the Intermediate Product 1-(4-fluorophenyl)-3-[6-(N-tert-butoxycarbonyl)-amino]hexyl-2-thiourea Method C, Step 1

The product was prepared starting from a solution of p-fluorophenylisothiocyanate (641 mg, 4.19 mmol) in CH$_2$Cl$_2$ (15 mL), to which was added N-(tert-butoxycarbonyl)-diaminohexane (1.36 g, 6.29 mmol). The reaction mixture was left under stirring at room temperature for 12 hours. At the end of this period, the solution was concentrated to dryness and the residue was purified by silica gel chromatography using AcOEt/propyl ether 1:1 as eluent to give 1.32 g of product as a pale yellow solid (yield: 85%). M.p.: 127-129° C.; IR CHCl$_3$ ν 3312, 2931, 1686, 1533, 1507, 1365, 1167 cm$^{-1}$; $^1$H-NMR (CDCl$_3$) δ: 7.98 (1H, brs); 7.18 (2H, t, J=8.3 Hz); 7.06 (2H, t, J=8.3 Hz); 6.04 (1H, brs); 4.57 (1H, brs); 3.55 (2H, q, J=6.6 Hz); 3.03 (2H, t, 6.6 Hz); 1.71-1.30 (17H, m).

Preparation of the Intermediate Product N-(4-fluorophenyl)-N'-[6-(N"-tert-butoxycarbonyl)amino]hexyl carbodiimide Method C, Step 2

The product was prepared starting from a solution of 1-(4-fluorophenyl)-3-[6-(N-tert-butoxycarbonyl)-amino]hexyl-2-thiourea (1.3 g, 3.5 mmol) in CH$_2$Cl$_2$ (20 mL) to which were added 2-chloro-N-methylpyridinium iodide (1.5 g, 6.0 mmol) and DIPEA (1.8 mL, 10.71 mmol). The reaction mixture was left under stirring at room temperature for 12 hours. At the end of this period, the mixture was filtered on a Buchner funnel and the solid was washed with CH$_2$Cl$_2$; the filtrate was extracted with H$_2$O, the organic phase was washed with NaCl s.s. and dried on anhydrous Na$_2$SO$_4$. The residue was purified by silica gel chromatography using propyl ether/Et$_2$O 1:9 as eluent to give 1.0 g of product as a colourless oil (yield: 90%). IR CHCl$_3$ ν 2928, 2134, 1690 cm$^{-1}$; $^1$H-NMR (CDCl$_3$) δ: 7.02-6.92 (4H, m); 4.51 (1H, brs); 3.36 (2H, t, J=6.5 Hz); 3.03 (2H, q, J=6.5 Hz) 1.66-1.60 (2H, m); 1.56-1.28 (15H, m).

Preparation of the intermediate product N-(4-fluorophenyl)-N'-[6-(N"-tert-butoxycarbonyl) amino]hexyl-4-methyl-1-piperazino-carboximidamide Method C, Step 3

The product was prepared starting from a solution of N-(4-fluorophenyl)-N'-[6-(N"-tert-butoxycarbonyl)amino] hexyl-carbodiimide (125 mg, 0.37 mmol) in toluene (4 mL) to which was added N-methylpiperazine (44.2 mg, 0.44 mmol). The reaction was brought to 50° C. and kept at that temperature for 4 hours. At the end of this time period, 3-(isothiocyano)-propyl silica gel (250 mg, 0.12-0.35 mmol) was added to the solution. The mixture was kept at 50° C.

for 12 hours. At the end of this period, the mixture was filtered on a Gooch funnel, and the solution was evaporated to dryness, obtaining 145 mg of product as a yellow oil (yield: 92%). IR CHCl$_3$ ν 3453, 1707, 1620, cm$^{-1}$; $^1$H-NMR (CDCl$_3$) δ: 6.87 (2H, t, J=8.7 Hz); 6.65 (2H, t, J=8.6 Hz); 4.62 (1H, brs); 3.16 (4H, t, J=4.5 Hz); 2.99 (2H, q, J=7.0 Hz); 2.88 (2H, t, J=7.0 Hz); 2.35 (4H, t, J=4.5 Hz); 2.23 (3H, s); 1.42-1.17 (17H, m).

Preparation of N-(4-fluorophenyl)-N'-(6-aminohexyl)-4-methyl-1-piperazinocarboximidamide (ST 2601)

Method C, Step 4

The product was prepared starting from a solution of N-(4-fluorophenyl)-N'-[6'-(N''-tert-butoxycarbonyl)-amino]hexyl-4-methyl-1-piperazinocarboximidamide (120 mg, 0.27 mmol) in CH$_2$Cl$_2$ (5 mL), to which was added trifluoroacetic acid (370 mg, 0.25 mL, 3.24 mmol). The solution was left at room temperature for 4 hours. At the end of this period, the solution was evaporated to dryness, giving 150 mg of product as an oil (yield: 100%). $^1$H-NMR (CD$_3$COCD$_3$) □: 10.26 (1H, br); 7.29-7.15 (4H, m); 3.96-3.49 (6H, m); 3.41-3.30 (6H, m); 2.94 (3H, s) 1.60-1.26 (6H, m); HPLC: Zorbax Eclipse XDB-C8 column (5 μm, 150×4.6 mm); mobile phase MeOH:H$_2$O 60:40, flow 0.5 mL/min; detector: UV 254 nm, RT=2.36 min.

EXAMPLE 7

Preparation of N-(4-fluorophenyl)-N'-(6-aminohexyl]-1-piperidino-carboximidamide (ST 2602)

Preparation of the Intermediate Product 1-(4-fluorophenyl)-3-[6-(N-tert-butoxycarbonyl)-amino]hexyl-2-thiourea Method C, Step 1

The product was prepared starting from a solution of p-fluorophenylisothiocyanate (641 mg, 4.19 mmol) in CH$_2$Cl$_2$ (15 mL), to which was added N-(tert-butoxycarbonyl)-diaminohexane (1.36 g, 6.29 mmol. The reaction mixture was left under stirring at room temperature for 12 hours. At the end of this period, the solution was concentrated to dryness and the residue was purified by silica gel chromatography using AcOEt/propyl ether 1:1 as eluent to give 1.32 g of product as a pale yellow solid (yield: 85%). M.p.: 127-129° C.; IR CHCl$_3$ ν 3312, 2931, 1686, 1533, 1507, 1365, 1167 cm$^{-1}$; $^1$H-NMR (CDCl$_3$) δ: 7.98 (1H, brs); 7.18 (2H, t, J=8.3 Hz); 7.06 (2H, t, J=8.3 Hz); 6.04 (1H, brs); 4.57 (1H, brs); 3.55 (2H, q, J=6.6 Hz); 3.03 (2H, t, J=6.6 Hz); 1.71-1.30 (17H, m).

Preparation of the Intermediate Product N-(4-fluorophenyl)-N'-[6-(N''-tert-butoxycarbonyl)-amino]hexyl carbodiimide Method C, Step 2

The product was prepared starting from a solution of 1-(4-fluorophenyl)-3-[6-(N-tert-butoxycarbonyl)-amino]hexyl-2-thiourea (1.3 g, 3.5 mmol) in CH$_2$Cl$_2$ (20 mL) to which were added 2-chloro-N-methylpyridinium iodide (1.5 g, 6.0 mmol) and DIPEA (1.8 mL, 10.71 mmol). The reaction mixture was left under stirring stir at room temperature for 12 hours. At the end of this period, the mixture was filtered on a Buchner funnel and the solid was washed with CH$_2$Cl$_2$; the filtrate was extracted with H$_2$O, and the organic residue was then washed with a saturated solution of NaCl and dried on anhydrous Na$_2$SO$_4$. The residue was purified by silica gel chromatography using propyl ether/ Et$_2$O 1:9 as eluent to give 1.0 g of product as a colourless oil (yield: 90%). IR CHCl$_3$ ν 2928, 2134, 1690, cm$^{-1}$; $^1$H-NMR (CDCl$_3$) δ: 7.02-6.92 (4H, m); 4.51 (1H, brs); 3.36 (2H, t, J=6.5 Hz); 3.03 (2H, q, J=6.5 Hz); 1.66-160 (2H, m); 1.56-1.28 (15H, m).

Preparation of the Intermediate Product N-(4-fluorophenyl)-N'-[6-(N''-tert-butoxycarbonyl)-amino]hexyl-1-piperidinocarboximidamide Method C, Step 3

The product was prepared starting from a solution of N-(4-fluorophenyl)-N'-[6-(N''-tert-butoxycarbonyl)-amino] hexyl carbodiimide (150 mg, 0.44 mmol) in toluene (5 mL) to which was added piperidine (44.7 mg, 0.53 mmol). The reaction was brought to 50° C. and kept at that temperature for 4 hours. At the end of that period, 3-(isothiocyano)-propyl silica gel (250 mg, 0.12-0.35 mmol) was added to the solution, and the mixture was kept at 50° C. for 12 hours. At the end of that period, the mixture was filtered on a Gooch funnel and the solution was evaporated to dryness, obtaining 145 mg of product as a yellow oil (yield: 90%). IR CHCl$_3$ ν 3448, 1709, 1627, cm$^{-1}$; $^1$H-NMR (CDCl$_3$) δ: 6.87 (2H, t, J=7.3 Hz); 6.69 (2H, t, J=7.3 Hz); 4.58 (1H, brs); 3.40 (1H, brs); 3.10-2.88 (8H, m); 1.52-1.10 (23H, m).

Preparation of N-(4-fluorophenyl)-N'-(6-aminohexyl)-1-piperidino-carboximidamide (ST 2602)

Method C, Step 4

The product was prepared starting from a solution of N-(4-fluorophenyl)-N'-[6-(N'''tert-butoxycarbonyl)-amino] hexyl-1-piperidinocarboximidamide (120 mg, 0.28 mmol) in CH$_2$Cl$_2$ (5 mL), to which was added trifluoroacetic acid (370 mg, 0.25 mL, 3.24 mmol). The solution was left at room temperature for 4 hours. At the end of this period, the solution was evaporated to dryness giving 120 mg of product as an oil (yield: 100%). $^1$H-NMR (CD$_3$COCD$_3$) δ: 8.17 (1H, brs); 7.20-7.12 (4H, m); 3.75-3.68 (2H, m); 3.50-3.26 (6H, m); 3.02-2.99 (2H, m); 2.49 (2H, brs); 1.81-1.01 (12H, m); HPLC: Zorbax Eclipse XDB-C8 column (5 μm, 150×4.6 mm); mobile phase MeOH:H$_2$O 60:40, flow 0.5 mL/min; detector: UV 254 nm, RT=2.32 min.

EXAMPLE 8

Preparation of N-(4-fluorophenyl)-N'-(4-aminobutyl)-4-methyl-1-pipiperazinocarboximidamide (ST2658)

Preparation of the Intermediate Product 11-(4-fluorophenyl)-3-[4-(N-tert-butoxycarbonyl)-amino]butyl-2-thiourea Method C, Step 1

The product was prepared starting from a solution of p-fluorophenylisothiocyanate (272 mg, 1.78 mmol) in CH$_2$Cl$_2$ (10 mL), to which was added N-(tert-butoxycarbonyl)-diaminobutane (502 mg, 2.67 mmol). The reaction mixture was left under stirring at room temperature for 5 hours. At the end of this period, the precipitate formed was filtered with a Buchner funnel and the solid was washed with petroleum ether (50 mL) obtaining 592 mg of product as a white solid (yield: 95%).M.p.: 152-153° C.; IR CHCl$_3$ ν 3294, 2924, 1699, 1166 cm$^{-1}$; $^1$H-NMR (CDCl$_3$) δ: 7.76 (1H, brs); 7.21 (2H, t); 7.09 (2H, t); 6.03 (1H, brs); 4.59 (1H, brs); 3.61 (2H, q, J=6.3 Hz); 3.10 (2H, q, J=6.3 Hz); 1.63-1.47 (4H, m); 1.39 (9H, s).

Preparation of the Intermediate Product N-(4-fluorophenyl)-N'-[4-(N''-tert-butoxycarbonyl)amino]butyl carbodiimide Method C, Step 2

The product was prepared starting from a solution of 1-(4-fluorophenyl)-3-[4-(N-tert-butoxycarbonyl)-amino]butyl-2-thiourea (580 mg, 1.69 mmol) in CH$_2$Cl$_2$ (15 mL) to which were added 2-chloro-N-methylpyridinium iodide (734 mg, 2.87 mmol) and DIPEA (0.86 mL, 5.07 mmol). The reaction mixture was left under stirring at room temperature for 12 hours. At the end of this period, the mixture was filtered on a Buchner funnel and the solid was washed with CH$_2$Cl$_2$; the filtrate was extracted with H$_2$O; the organic phase was then washed with a saturated solution of NaCl and dried on anhydrous Na$_2$SO$_4$. The residue was purified by silica gel chromatography using propyl ether/Et$_2$O 1:9 as eluent to give 441 mg of product as a colourless oil (yield: 85%). IR CHCl$_3$ ν 2979, 2132, 1708 cm$^{-1}$; $^1$H-NMR (CDCl$_3$) δ: 6.98-6.83 (4H, m); 4.68 (1H, brs); 3.35 (2H, t, J=6.2 Hz); 3.08 (2H, t, J=6.2 Hz); 1.65-1.48 (4H, m); 1.36 (9H, s).

Preparation of the Intermediate Product N-(4-fluorophenyl)-N'-[4-(N''-tert-butoxycarbonyl)amino]butyl-4-methyl-1-piperazinocarboximidamide Method C, Step 3

The product was prepared starting from a solution of N-(4-fluorophenyl)-N'-[4(N''-tert-butoxycarbonyl)-amino] butyl carbodiimide (175 mg, 0.56 mmol) in toluene (4 mL) to which was added N-methylpiperazine (67.7 mg, 0.67 mmol). The reaction was brought to 50° C. and kept at that temperature for 4 hours. At the end of this period, 3-(isothiocyano)-propyl silica gel (250 mg, 0.12-0.35 mmol) was added to the solution; the mixture was held at 50° C. for 12 hours. At the end of this period, the mixture was filtered on a Gooch funnel, and the solution was evaporated to dryness, obtaining 145 mg of product as a yellow oil (yield: 90%). IR CHCl$_3$ ν 3451, 1710, 1624, cm$^{-1}$; $^1$H-NMR (CDCl$_3$) δ: 6.87 (2H, t, J=8.6 Hz); 6.69 (2H, t, J=8.7 Hz); 4.64 (1H, brs); 3.17 (4H, t, J=4.7 Hz); 3.01-2.92 (4H, m); 2.36 (4H, t, J=4.7 Hz); 2.24 (3H, s); 1.37-1.19 (13H, m).

Preparation of N-(4-fluorophenyl)-N'-(4-aminobutyl)-4-methyl-1-piperazinocarboximidamide (ST2658)

Method C, Step 4

The product was prepared starting from a solution of N-(4-fluorophenyl)-N'-[4-(N''-tert-butoxycarbonyl)amino] butyl-4-methyl-1-piperazinocarboximidamide (210 mg, 0.51 mmol) in CH$_2$Cl$_2$ (5 mL), to which was added trifluoroacetic acid (370 mg, 0.25 mL, 3.24 mmol). The solution was left at room temperature for 4 hours. At the end of this period, the solution was evaporated to dryness, giving 268 mg of product as an orange-coloured oil (yield: 100%). $^1$H-NMR (CD$_3$COCD$_3$) δ: 7.37-7.12 (4H, m); 4.23 (1H, brs); 3.79-3.77 (4H, m); 3.53-3.29 (4H, m); 3.03 (4H, m); 2.96 (3H, s); 1.65-1.43 (4H, m); HPLC: Zorbax Eclipse XDB-C8 column (5 μm, 150×4.6 mm); mobile phase MeOH:H$_2$O 60:40, flow 0.5 mL/min; detector: UV 254 nm, RT=3.01 min.

EXAMPLE 9

Preparation of N-(γ,γ-dimethylallyl)-N'-(5-aminopentyl)guanidine methane sulphonate (ST2574)

Preparation of the intermediate product 4-[N$^2$,N$^3$-bis(ter-butoxy-carbonyl-N$^3$-(γ,γ-dimethylallyl)-guanidino]-1-aminopentane Method A, Step 2

A solution of N-(γ,γ-dimethylallyl)-N,N'-bis(ter-butoxycarbonyl)-S-methylthiourea, prepared as described in example 1, (250 mg, 0.97 mmol) in THF (7.5 mL) was added dropwise to a solution of 1,5-diaminopentane (297 mg, 2.9 mmol) in 1 mL of THF. The reaction was brought to 50° C. and kept at that temperature for 3 hours. The reaction mixture was concentrated at reduced pressure and the residue was dissolved in a mixture of CHCl$_3$/NaHCO$_3$ 10%; the two phases were separated and the aqueous phase was extracted with CHCl$_3$. The pooled organic phases were dried on anhydrous Na$_2$SO$_4$. After evaporation of the solvent in vacuo the residue was purified by chromatography using CHCl$_3$/NEt$_3$ 5% as eluent to give 250 mg of product as a glassy white solid (yield: 70%). IR (CHCl$_3$) ν 3248, 1721, 1627 cm$^{-1}$, $^1$H-NMR (CDCl$_3$) δ 5.17 (1H, t, J=7.0 Hz); 4.20 (2H, d, J=7.0 Hz); 3.27, 2.78 (2H each, d); 1.70-1.30 (12H, m); 1.50, 1.46 (9H each, m).

Preparation of N-(γ,γ-dimethylallyl)-N'-(5-aminopentyl) guanidine methane sulphonate (ST2574)

Method A, Step 3

The product was prepared starting from a solution of 4-[N$^2$,N$^3$-bis(ter-butoxycarbonyl-N$^3$-(γ,γ-dimethylallyl)-guanidino]-1-amino-pentane (250 mg, 0.60 mmol) in anhydrous dioxane (25 mL) containing methane-sulphonic acid (57.6 mg, 38.9 μL, 0.60 mmol); the solution was left at reflux temperature in an N$_2$ atmosphere for 3 hours. The solution was then cooled and concentrated to dryness in vacuo, and the yellow-brown amorphous solid obtained was washed with ethyl ether, giving 110 mg of product as a rubbery amorphous solid (yield: 62%). $^1$H-NMR(CD$_3$OD) δ 5.20-5.28 (1H, m), 3.74-3.93 (2H, dd); 3.11-3.26 (4H, m), 2.93-2.99 (2H, m), 2.68 (3H, s), 1.66-1.84 (6H, m), 1.39-1.49 (4H, m).

EXAMPLE 10

Preparation of N-(γ,γ-dimethylallyl)-N'-(7-aminoheptyl)guanidine methane sulphonate (ST2575)

Preparation of the Intermediate Product 4-[N$^2$,N$^3$-bis(ter-butoxy-carbonyl-N$^3$-γ,γ-dimethylallyl)-guanidino]-1-aminoheptane Method A, Step 2

A solution of N-(γ,γ-dimethylallyl)-N,N'-bis(ter-butoxycarbonyl)-S-methylthiourea, prepared as described in example 1, (350 mg, 0.97 mmol) in THF (9.5 mL) was added dropwise to a solution of 1,7-diaminoheptane (379 mg, 2.9 mmol) in 1 mL of THF. The reaction was brought to 50° C. and held at that temperature for 3 hours. The reaction mixture was concentrated at reduced pressure and the residue dissolved in a mixture of CHCl$_3$/NaHCO$_3$ 10%; the two phases were separated and the aqueous phase was extracted with CHCl$_3$. The pooled organic phases were dried on anhydrous Na$_2$SO$_4$. After evaporation of the solvent in vacuo, the residue was purified by chromatography using CHCl$_3$/NEt$_3$ 5% as eluent to give 200 mg of product as a glassy white solid (yield: 50%). IR (CHCl$_3$) υ 3248, 1721, 1627 cm$^{-1}$, $^1$H-NMR(CDCl$_3$) δ 5.15 (1H, t, J=7.2 Hz); 4.18 (2H, d, J=7.2 Hz); 3.25, 2.78 (2H each, d, J=6.9 Hz), 1.70-1.30 (16H, m); 1.50, 1.46 (9H each).

Preparation of N-(γ, γ-dimethylallyl)-N'-(7-aminoheptyl) guanidine methane sulphonate (ST2575)

Method A, Step 3

The product was prepared starting from a solution of 4-[N$^2$,N$^3$-bis(ter-butoxycarbonyl-N$^3$-(γ,γ-dimethylallyl)-guanidino]-1-amino-heptane (200 mg, 0.45 mmol) in anhydrous dioxane (20 mL) containing methane-sulphonic acid (43.2 mg, 29 μL, 0.45 mmol). The solution was left at reflux temperature in an N$_2$ atmosphere for 3 hours. The solution was then cooled and concentrated to dryness in vacuo, and the yellowy-brown amorphous solid obtained was washed with ethyl ether, giving 130 mg of product as a rubbery amorphous solid (yield: 85%). $^1$H-NMR(CD$_3$OD) δ 5.26-5.20 (1H, m), 3.90-3.73 (2H, dd), 3.15-3.27 (4H, m), 2.93-2.99 (4H, m), 2.68 (3H, s), 1.84-1.66 (6H, m), 1.52-1.39 (6H, m).

EXAMPLE 11

Serum-glucose-lowering and Appetite-lowering Activity of Guanidine Compounds.

Mutations in laboratory animals have made it possible to develop models presenting non-insulin-dependent diabetes associated with obesity, hyperlipidaemia and insulin resistance and that enable us to test the efficacy of new antidiabetes compounds (Reed and Scribner, *Diabetes, obesity and metabolism* 1: 75-86, 1999).

The genetically diabetic mouse models widely used in these studies are the ob/ob mouse and the db/db mouse.

The genetic basis of these models is a defect in the leptin gene (ob/ob mouse) or in the leptin receptor (db/db mouse), which causes leptin resistance and leads to overeating, obesity, hyperinsulinaemia and insulin resistance, with subsequent symptoms of insufficient insular secretion and hyperglycaemia (Hummel et al, *Science* 153: 1127-1128, 1996; Coleman, *Diabetologia* 14: 141-148, 1978; Kodama et al., *Diabetologia* 37: 739-744, 1994; Zhang et al., *Nature* 372: 425-432, 1994; Halaas et al., *Science* 269: 543-546, 1995; Chen et al., *Cell* 84: 491-495, 1996).

Since hyperglycaemia is accompanied by obesity and insulin resistance, ob/ob and db/db mice present characteristics that resemble those of type 2 diabetes in human subjects.

The C57BL/KsJ db/db mice used in the experiments reported here below were supplied by Jackson Lab (via Ch. River).

The literature data (Meglasson et al., *J Pharmacol Exp Ther* 266: 1454-1462, 1993) indicate that the oral metformin dose of 900 mg/kg/day is effective in producing a 50% reduction in hyperglycaemia in the KKAy mouse, which is a model of obese, hyperinsulinaemic and hyperglycaemic genetic diabetes similar to the db/db and ob/ob mice.

In laboratory experiments it has been observed that the oral metformin dose of 600 mg/kg/day is effective in reducing hyperglycaemia in the ob/ob mouse by 22%.

The literature data also show that the LD$_{50}$ of metformin in the rat is 300 mg/kg subcutaneously and 1000 mg/kg for oral administration (The Merck Index 12th ed., page 1014).

On the basis of this information, metformin was administered to the db/db mice in the experiment, in standard environmental conditions and with the mice on a normal diet, (4 RF 21, Mucedola) at the dose of 100 mg/kg and the compounds according to the invention at the dose of 25 mg/kg, subcutaneously, twice daily for 4 days.

On day 5, in postabsorption conditions (fasting from 9.00 a.m. to 4.00 p.m.) and 7 hours after the last treatment, blood samples were taken from the caudal vein for monitoring serum glucose.

By way of an example, we report the results for compound ST2370 according to the invention which show a significant degree of serum-glucose-lowering activity at the experimental dose used, which, in contrast, is not observed after administration of metformin at a 4-fold higher dose (Table 1).

Moreover, the compounds according to the invention proved capable of reducing the uptake of food and water, as shown by the data for the compounds ST2370 and ST2369 which are provided here by way of examples (Table 2).

TABLE 1

Glucose levels in male db/db mice treated with the products subcutaneously twice daily (8.30 a.m. and 5.30 p.m.) for 4 days, in postabsorption conditions (fasting from 8.00 a.m. to 5.30 p.m.) and 8 hours after the last treatment. Variation (%) vs Control.

| Groups | Dose mg/kg | Glucose % |
|---|---|---|
| CTR | — | 100 |
| Metformin | 100 | 104 |
| ST2370 | 25 | 69 □ |

Number of cases per group: 4.
Student's t-test: p indicates P < 0.05 vs Control.

TABLE 2

Consumption of water and food by male db/db mice treated with the products subcutaneously twice daily (8.30 a.m. and 5.30 p.m.) for 4 days. Variation (%) vs Control.

| Groups | Dose mg/kg | Food % | Water % |
|---|---|---|---|
| CTR | — | 100 | 100 |
| Metformin | 100 | 119 | 113 |
| ST2369 | 25 | 63 | 47 |
| ST2370 | 25 | 81 | 47 |

Number of cases per group: 4 (single cage).

The objects of the present invention are pharmaceutical compositions containing as their active ingredient at least one formula (I) compound, either alone or in combination with one or more formula (I) compounds, or, said formula (I) compound or compounds in combination with other active ingredients useful in the treatment of the diseases indicated in the present invention, for example, other products with serum-glucose-lowering and serum-lipid-lowering activity; also in separate dosage forms or in forms suitable for combined therapies. The active ingredient according to the present invention will be in a mixture with suitable vehicles and/or excipients commonly used in pharmacy, such as, for instance, those described in "Remington's Pharmaceutical Sciences Handbook", latest edition. The compositions according to the present invention will contain a therapeutically effective amount of the active ingredient. The doses will be decided by the expert in the sector, e.g. the clinician or primary care physician according to the type of disease to be treated and the patient's condition, or concomitantly with the administration of other active ingredients. By way of an example, dosages ranging from 0.1 to 4000 mg/day can be indicated, preferably 100-3000 mg/day.

Examples of pharmaceutical compositions are those that allow administration orally or parenterally—intravenous, intramuscular, subcutaneous, transdermal. Suitable pharmaceutical compositions for the purpose are tablets, rigid or soft capsules, powders, solutions, suspensions, syrups, and solid forms for extempore liquid preparations. Compositions for parenteral administration are, for example, all the forms which are injectable intramuscularly, intravenously, subcutaneously, or in the form of solutions, suspensions or emulsions. Liposomal formulations should also be mentioned. Other forms are tablets for the controlled release of the active ingredient, or for oral administration, tablets coated with appropriate layers, microencapsulated powders, complexes with cyclodextrin, and depot forms, for example, subcutaneous ones, such as depot injections or implants.

The invention claimed is:

1. A compound of the formula:

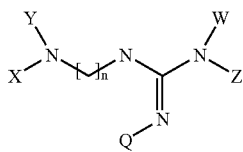

I in which:
Z is a saturated or unsaturated alkyl containing from 1 to 7 carbon atoms;
W is equal to H or, together with Z, may form a cycle, optionally containing one or more heteroatoms;
n=4-7;
Q is selected from the Z groups listed above;
X and Y are the same or different and are selected from the Z groups listed above;
X may be a substituted amino-imino of the formula:

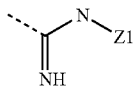

where Z1 is selected from the Z groups listed above;
or X is an R—CO group and, with nitrogen, may form a group:

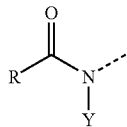

where R is selected from the Z groups listed above or —OZ or —NZ;
and their pharmacologically acceptable salts, the racemic mixtures, the single enantiomers, stereoisomers and geometric isomers and tautomers,
with the proviso that the formula (I) compound is not N-(4-aminobutyl)-N'-(γ,γ-dimethylallyl)guanidine methane sulphonate (ST2369) or N-(γ,γ-dimethylallyl) guanidine methane sulphonate (ST 2527).

2. A compound according to claim 1, in which X and Y are equal to hydrogen.

3. A compound according to claim 1, selected from the group consisting of:

N-(6-aminohexyl)-N'-(γ,γ-dimethylallyl)guanidine methane sulphonate (ST2370);
N-allyl-N'-(4-aminobutyl)guanidine dichlorhydrate (ST2525);
1,4-bis-[N-(γ,γ-dimethylallyl)guanidino]-butane dimethane sulphonate (ST2526);
N-(γ,γ-dimetilallil)-N'-(5-amminopentil)guanidina metansolfonata (ST2574); and
N-(γ,γ-dimetilallil)-N'-(7-amminoeptil)guanidina metansolfonata (ST2575).

4. A pharmaceutical composition containing at least one compound according to claim 1 in a mixture with one or more pharmaceutically acceptable vehicles and/or excipients.

5. A composition according to claim 4, in the form of tablets, rigid or soft capsules, powders, solutions, suspensions, syrups, solid forms for extempore liquid preparations, emulsions, liposomal preparations, forms for the controlled release of the active ingredient, tablets coated with appropriate layers, microencapsulated powders, complexes with cyclodextrin, depot forms, depot injections or implants.

6. A composition according to claim 5, which can be administered orally or parenterally.

7. A method for lowering serum glucose and serum lipids comprising administering to a subject in need thereof a compound of claim 1.

8. The method according to claim 7, in which the compound is selected from the group consisting of:

N-(6-aminohexyl)-N'-(γ,γ-dimethylallyl)guanidine methane sulphonate (ST2370);
N-allyl-N'-(4-aminobutyl)guanidine dichlorhydrate (ST2525);
1,4-bis-[N-(γ,γ-dimethylallyl)guanidino]-butane dimethane sulphonate (ST2526);
N-(4-aminobutyl)-N'-(γ,γ-dimethylallyl)guanidine methane sulphonate (ST2369);
N-(γ,γ-dimethylallyl)guanidine methane sulphonate (ST2527).

9. A method for treating diabetes, type 2 diabetes, syndrome X, insulin resistance, hyperlipidaemias and obesity comprising administering to a subject in need thereof a compound according to claim 1.

10. The method according to claim 9, in which the compound is selected from the group consisting of:

N-(6-aminohexyl)-N'-(γ,γ-dimethylallyl)guanidine methane sulphonate (ST2370);
N-allyl-N'-(4-aminobutyl)guanidine dichlorohydrate (ST2525);
1,4-bis-[N-(γ,γ-dimethylallyl)guanidino]-butane dimethane sulphonate (ST2526);
N-(γ,γ-dimetilallil)-N'-(5-amminopentil)guanidina metansolfonata (ST2574); and
N-(γ,γ-dimetilallil)-N'-(7-amminoeptil)guanidina metansolfonata (ST2575).

* * * * *